United States Patent [19]

Pickart

[11] Patent Number: 4,760,051
[45] Date of Patent: Jul. 26, 1988

[54] USE OF GHL-CU AS A WOUND-HEALING AND ANTI-INFLAMMATORY AGENT

[76] Inventor: Loren R. Pickart, 15232 SE. 48th Dr., Bellevue, Wash. 98006

[21] Appl. No.: 694,430

[22] Filed: Jan. 24, 1985

[51] Int. Cl.$^4$ ............................................. A61K 37/14
[52] U.S. Cl. ......................................... 514/6; 514/18; 514/886; 514/887; 514/936; 424/140
[58] Field of Search ..................... 514/18, 6, 886, 887, 514/936; 424/140

[56] References Cited

U.S. PATENT DOCUMENTS 3,551,554 12/1970 Herschler .............................. 424/59
4,440,788 4/1984 Terayama et al. .................. 514/616

OTHER PUBLICATIONS

Raju et al., "Ceruloplasmin, Copper Ions, and Angiogenesis38", JNCI 69:1183–1188, 1982.
Pickart, "The Biological Effects and Mechanism of Action of the Plasma Tripeptide Glycyl-1-Histidyl-1-Lysine, *Lymphokines* 8:425–446, 1983.
Poole and Zetter, "Stimulation of Rat Peritoneal Mast Cell Migration by Tumor–Derived Peptides, *Cancer Research* 43: 5857–5861, 1983.
Freedman et al., "Structure of the Glycyl-1-Histidyl-1-Lysine: Copper(II) Complex in Solution", *Biochemistry* 21:4540–4544, 1982.
Kwa et al., "PMR Studies of Ca(II) and Zn(II)—Interaction with GHL and Related Peptides", *Peptides: Structure and Function* 8:805–808, 1983.
Perkins et al., "The Structure of a Copper Complex of the Growth Factor GHL at 1.1 Resolution", *Inorganica Chimica Acta* 82:93–99, 1984.
Kwa, "GHL: Synthesis of Analogs and NMR Studies", Thesis, 1983.
Loker, "Synthesis of Blood Serum Peptide Cell Growth Factors", Thesis, 1980.
Chem. Abstracts Citation of Pickart et al. 93:1155m 1980.
Chem. Abstracts Citation of Williams et al. vol. 94:25451b 1981.
Pickart, *Nature* vol. 288, pp. 715–717 1980.
Mochida Pharmaceutical Co Ltd., cited in Chem. Abstracts vol. 94:145386f 1981.

*Primary Examiner*—J. R. Brown
*Assistant Examiner*—Jacqueline M. Stone

[57] ABSTRACT

A method of enhancing the wound-healing process in animals utilizing glycyl-1-histidyl-1-lysine: copper(II) (GHL-Cu) is disclosed. GHL-Cu functions as a superoxide dismutase which detoxifies tissue-damaging oxygen radicals, but does not evoke an antigenic response. A method of treating inflammatory conditions in animals and a method of reducing the traumatic effects in animals occurring subsequent to major tissue damage utilizing GHL-Cu is also disclosed.

20 Claims, No Drawings

USE OF GHL-CU AS A WOUND-HEALING AND ANTI-INFLAMMATORY AGENT

TECHNICAL FIELD

The present invention relates to the treatment of wounds in animals in general, and more specifically, to the use of a peptide having human superoxide dismutase activity, glycyl-L-hystidyl-L-lysine: copper(II), for enhancing the wound-healing process.

BACKGROUND ART

Mechanisms of wound healing and tissue repair in humans and in other animals are often inadequate and incomplete. Wound healing is often substantially impaired in the elderly, in cancer patients after chemotherapy or radiation treatments, in persons with diabetes, and in individuals suffering from severe burns. The lesions caused by auto-immune diseases such as Krohn's disease or osteoarthritis are also characterized by slow and deficient healing. In general, poorly healed wounds are characterized by necrotic regions which rapidly become infected, causing pain and suffering to the person and requiring additional medical treatment. Even when such wounds finally heal, the "wound area" is often devoid of the ability to respond to tactile stimulus and is often filled with excessive deposits of collagen that lead to uncleared scarring.

Wound healing is a highly precise biological process initially exemplified by an invasion of cells of the immunological system and fibroblastic cells which secrete the structural protein collagen into the wounded area. Later, blood and lymphatic vessels reform, and nerve axions infiltrate the wound area. A currently incomplete understanding of the biological processes regulating the healing process if reflected by the relative inadequacy of present treatment methods.

Current methods of treatment of wounds include the use of a type of nerve growth factor to accelerate the wound healing process (U.S. Pat. No. 4,287,184), a mixture of albumin-freed cap serum and vasodilatory peptides (kinins) (U.S. Pat. No. 4,177,261) and the use of partially digested bovine casein, polyvinyl pyrrolidine and carrageenan as a healing aid (U.S. Pat. No. 3,558,770). Other treatments include the use of emulsified aqueous mixtures of bovine gelatin, sucrose, corn syrup, oatmeal, and other salts in order to provide a protective covering for wounds, as in U.S. Pat. No. 3,767,784, and the use of egg shell membrane products, as in U.S. Pat. No, 3,194,732.

With regard to all of the above cited wound-healing formulations, immunological considerations suggest that the foreignness of the components in these formulations would most likely elicit an antibody recognition and subsequent inflammatory response in any animal except the donor species. In hypersensitive or allergic animals or human patients, such responses can often be lethal.

The most promising compositions to date which have proven to accelerate the healing of a wide variety of wounds and tissue injury are a class of compounds called superoxide dismutases, compounds that possess a biochemical ability to detoxify a highly-reactive tissue-damaging oxygen radical called superoxide anion. The healing of many types of traumatic tissue damage and of aging associated degenerative conditions is delayed by the excessive production of superoxide anion. After wounding or dramatic tissue injury, cells of the immune system invade the damaged area and secrete copious quantities of toxic oxygen radicals to kill invading bacteria. In a similar manner, in auto-immune diseases, the immunological cells also secrete oxygen radicals into the afflicted area, ostensibly to kill infective organisms, and thereby induce tissue damage and localized inflammation.

Often in cases of impaired healing, the production of superoxide anion further damages tissues and brings in a new influx of immunological cells, thereby creating a vicious circle of damaging events which can greatly delay the normal sequence within the healing process. To obtain proper healing of damaged tissue, it is generally necessary to terminate the production of superoxide anion in the afflicted area.

A number of biological and synthetic molecules catalyze the breakdown and toxification of superoxide anion, some of which have proven to possess clinically useful properties that promote healing and reduce inflammation. However, all such molecules have substantial deficiencies which sharply limit their clinical efficacy.

One approach has been to use certain low molecular weight copper chelates, such as salicylate-copper or diisopropylsalicylate-copper, which possess superoxide dismutase activity. While these complexes also possess anti-inflammatory and healing actions, they tend to dissociate after injection, since the binding affinity of the organic component for copper is too low to retain the copper under physiological conditions. In addition, these small copper complexes tend to be poorly soluble under aqueous conditions and must be administered with tissue-irritating solubilizing agents. Another of these copper chelates, the penicillamine-copper complex, often produces skin rashes and a personality change known as "penicillamine psychosis."

Another compound exhibiting superoxide dismutase activity, with a molecular weight of approximately 33,000, is the copper and zinc chelate known as Orgotein. Orgotein possesses anti-inflammatory and anti-trauma properties, and is thought to accelerate the healing of hemorrhoids, frost bite, skin abrasions, soft tissue injuries, and tissue damage associated with auto-immune diseases such as arthritis and Krohn's disease. Orgotein has been isolated from bovine tissue as described in U.S. Pat. Nos. 3,758,682 and 3,832,338 and esterified Orgotein has been described in U.S. Pat. No. 4,022,888. However, Orgoteins evoke an antigenic response in humans, and when therapeutically applied, exert their action in the extra-cellular tissue compartment as opposed to penetrating into the cells themselves.

Consequently, there exists a need in the art for an effective, non-toxic method of enhancing the wound healing process and reducing inflammation, which further does not evoke an antigenic response.

DISCLOSURE OF INVENTION

Briefly stated, the present invention discloses an improved method for enhancing the wound healing process in animals comprising administering to the animal a therapeutically effective amount of a composition containing glycyl-L-histidyl-L-lysine; copper(II). The composition may be applied through intravenous injection, topical application, or injection into the wound or the area surrounding the wound. Alternatively, the composition may further include an effective amount of dimethylsulfoxide.

Another aspect of the invention discloses a method of treating inflammatory conditions in animals comprising administering to the animal an anti-inflammatorily effective amount of a composition containing glycyl-L-histidyl-L-lysine: copper(II).

A further aspect of the invention discloses a method of inhibiting a rise in blood fibrinogen in injured animals comprising administering to the animal a therapeutically effective amount of a composition containing glycyl-L-histidyl-L-lysine: copper(II).

In addition, the invention discloses a method of reducing the traumatic effects in animals occurring subsequent to major tissue damage, comprising administering to the animal an anti-traumatic effective amount of a composition containing glycyl-L-histidyl-L-lysine: copper(II).

Other aspects of the invention will become evident upon reference to the following detailed description.

BEST MODE FOR CARRYING OUT THE INVENTION

As noted above, in the majority of wound-healing formulations, immunological considerations suggest that components used in the formulations will elicit antibody recognition and a subsequent inflammatory response in animals other than the donor species. Further, other alternatives, generally known as superoxide dismutases, tend to be either poorly soluble under aqueous conditions or evoke an antigenic response in the recipient.

Wound healing is a highly specific biological response involving many closely coordinated events which must be kept in balance for proper healing. Immunological cells must clear bacteria and damaged tissue from the wound, and then allow other processes to occur such as the re-epithelialization of the lost skin, deposition by fibroblastic cells of the structural protein collagen to provide temporary wound strength, the regrowth of nervous, blood vessel, and lymphatic networks, the contraction of the wound area, and the reestablishment of hair follicles in the newly-formed skin. If any process improperly predominates, healing is partial and inadequate. For example, excessive collagen deposition results in permanent scarring while excessive blood vessel growth may give rise to hemangioma.

Due to the complex interaction of various processes in the proper healing of wounds, a superior method for enhancing the wound healing process should include the proper maintenance of each of these processes without evoking an antigenic response. The present invention exemplifies such a method, and further provides other related advantages.

The present invention utilizes a therapeutically effectively amount of a composition consisting essentially of glycyl-L-histidyl-L-lysine: copper(II) (hereinafter referred to as "GHL-Cu") to enhance the wound healing process in aminals. The GHL-Cu utilized in this invention may be prepared from commercially available GHL (BACHEM, Torrence, Ca.). Commercially available GHL is about 95% pure, but often includes small amounts of mildly neurotoxic materials, and as such should be further purified.

GHL-Cu possesses significant superoxide dismutase activity at physiological pH and like other superoxide dismutases, has anti-inflammatory and wound healing properties. GHL-Cu also inhibits platelet aggregation and the production of the vasoconstrictive and thrombosis-inducing hormone, thromboxane.

GHL-Cu has many advantages over other pharmacologically active molecules having superoxide dismutase activity. In particular, it lacks Orgotein's antigenicity in humans, being both a human factor and being too small to elicit immunological recognition even after long term application. Further, it is readily water soluble and can be formulated in physiological buffers and in aqueous buffers containing dimethylsulfoxide. GHL-Cu is remarkably nontoxic in animals and stable under storage for at least four years. When administered in combination with dimethylsulfoxide, GHL-Cu is even more effective. GHL-Cu can function as a superoxide dismutase which detoxifies tissue-damaging oxygen radicals, and on a weight basis, it is twenty-times more potent than other clinically used superoxide dismutase molecules.

Further, GHL-Cu has advantages over low molecular weight molecules with superoxide dismutase activity due to its high affinity ($pK = 16.4$) for $Cu(II)$. This affinity is equivalent to the copper(II) transport site on the blood protein albumin ($pK = 16.2$) (Lau and Sarkar, Bio-Chem. J. 199: 649–656, 1981: Rainier and Rode, Inorg. Chim. Acta. 92: 1–7 (1984). This closeness of binding affinity ensures that the copper within GHL-CU will ultimately be cleared from the body and not lead to copper-overload toxicities.

In addition, GHL-Cu is soluble in quantities constituting over 25% of total solution weight, the solubility being variable through the addition of fatty groups to the molecule.

Similar to other superoxide dismutases, GHL-Cu reduces traumatic effects occurring subsequent to major tissue damage. For purposes of the present invention, the term "trauma" is defined to include effects occurring secondary to tissue injury, such as hyperfibrinogenemia, thromboembolism, shock, and loss of ambulatory desires.

To summarize the examples which follow, Example I demonstrates the topical application of a solution containing GHL-Cu in phosphate buffered saline to a wound. Example II describes the injection of GHL-Cu in phosphate buffered saline into tissue underlying a wound. Example III describes the injection of GHL-Cu in phosphate buffered saline into the outer circumference of a wound. Example IV describes the intravenous injection of GHL-Cu. Example V describes the intraperitoneal injection of GHL-Cu to reduce the trauma caused by tissue damage.

The following examples are offered by way of illustration, and not by way of limitation.

EXAMPLES

Preparation of GHL-Cu for Use in Animals

GHL was purified by dissolving in glass distilled water (50 mg/ml), then centrifuging at 20,000 g for 1 hour at 3 degrees centigrade. This removes poorly water soluble material remaining from the synthetic procedure. The supernatent is lyophilized, then passed through a Sephadex G-10 column at 3 degrees centigrade in a solvent of 0.5% acetic acid. The main peak that elutes behind the solvent front (monitored by absorption at 254 nanometers) is lyophized to dryness. GHL-Cu was prepared by combination of purified GHL with equimolar amounts of cupric acetate and sodium hydroxide, then precipitated by use of ethanol addition and low temperature by published methods (Perkins et al, *Inorg. Chim. Acta* 67: 93–99, 1984).

EXAMPLE I

In mice, incision wounds on the flanks (six 1.5 cm wounds per animal) were swabbed daily with either a solution containing GHL-Cu (100 micrograms per ml) in phosphate buffered saline (PBS) at a physiological pH, or PBS alone (12 animals each group). After five days, the wounds were scored 1.0 for complete closure, 0.5 for partial closure, and 0.0 for non-closure (Table 1).

TABLE 1

Effect of GHL-Cu on healing of wounds in mice.

| | Treatment Procedure | | Statistical |
|---|---|---|---|
| | Control | GHL-Cu | Significance |
| Score per wound | 0.21 ± 0.06 | 0.60 ± 0.11 | $p < 0.001$ |

EXAMPLE II

In pigs, skin and subcutaneous fat were excised (2.5 cm squares, three squares per side) from the upper back of Yorkshire pigs (10–12 Kg). On one side of the animal, GHL-Cu (50 micrograms) in PBS was injected into the underlying tissue while contralateral wounds were injected with PBS only. The wound area was covered with either collagen pads, dehydrated pig skin, or live pig skin (autologous skin graft). Wounds then were blanketed with Petrolatum gauze (Cheesborough Ponds, Greenwich, Ct.), then dry gauze. Adhesive tape and "Vetrap" (3M, St. Paul, Minn.) held the bandages in place. All animals received 100,000 units penicillin and 10 mg streptomycin per kilogram body weight.

GHL-Cu treated wounds healed faster than contralateral controls in all 10 pigs studies. By five days, treated wounds were measurably smaller than controls. This effect increased for three weeks post-wounding. At day 21, one treatment of GHL-Cu reduced the remaining wound size 64.9% (±22.1) in 14 wounds on eight pigs observed for this period (p=0.0023 for pooled data). This wound reduction occurred regardless of the type of wound coverage (Dehydrated pigskin (4 wounds)=−77.3% (±16.3), autologous skin grafts (2 wounds)=−82.0% (±1.4), gelatin film pads (6 wounds)=−58.8% (±16.4), no coverage on wound (2 wounds)=−41.5% (±3.5)).

EXAMPLE III

In rats, experiments started with the excision of a circular patch of skin from the back. The outer circumference of the wound was injected with either 50 micrograms GHL-Cu in PBS (10 rats) or PBS only for controls (6 rats) immediately after wounding, a second time at 24 hours, and a third time at 48 hours. Wounds were photographed at 5, 10, 15, and 25 days post-wounding. Data were analyzed by measurement of the wound circumference by computerized digitization of the perimeter of the wound in the photograph, then corrected with a scale bar to compensate for variations in magnification among the photographs. Time-point and group information were coded at the time of digitization to eliminate subjective bias (Table 2).

TABLE 2

Effect of GHL-Cu treatment on circumference of wounds.

| Time in days after wounding | Circumference of wound | | Significance of difference (P-value) |
|---|---|---|---|
| | GHL-Cu treated | Controls | |
| 5 | 5.17 ± 0.24 | 5.03 ± 0.20 | .29 |
| 10 | 3.04 ± 0.40 | 3.20 ± 0.36 | .22 |
| 15 | 1.60 ± 0.17 | 2.11 ± 0.35 | .0038 |
| 20 | .67 ± 0.48 | 1.53 ± 0.33 | .0005 |
| 25 | .20 ± 0.30 | 1.09 ± 0.17 | .00005 |

In an additional blinded study of these effects, the photographs of wounds at 25 days were judged by four surgeons as fully-healed or not fully healed, then the judgement statistically analyzed by the Fisher Exact Test (Table 3).

TABLE 3

Healing of wounds at 25 days.

| | GHL-Cu Treated Wounds | Control Wounds |
|---|---|---|
| Fully-healed | 6 | 0 |
| Not fully-healed | 4 | 6 |

Significance of difference, P=0.04.

EXAMPLE IV

Inflammatory paw edema was induced in rats by local injection of 1.5 mg carrageenan followed by intravenous injection of 0.5 mg GHL-Cu 30 minutes later. At 3 hours post-carrageenan, paw diameter was measured. Control rats received saline injections into the paws. There were 10 rats in each group (Table 4).

TABLE 4

Suppression of inflammation with GHL-Cu.

| | Paw Diameter (mm) |
|---|---|
| Control rats | 3.9 ± 0.3 |
| Carrageenan & saline | 6.9 ± 0.5 |
| Carrageenan & GHL-Cu | 5.0 ± 0.3 |

Statistical difference: (Carrageenan & saline) vs. (Carrageenan & GHL-Cu): $P < 0.001$

EXAMPLE V

GHL-Cu reduces trauma induced by tissue damage. In rats, tissue damage was induced by the injection of 0.25 ml sterile turpentine into the muscle mass of each rear leg. This procedure induces tissue damage, widespread intravascular coagulation, an acute-phase production of stress-associated proteins, and generalized shock effects.

These trauma effects were greatly minimized by the intraperitoneal injection of 2 mg GHL-Cu at times of 1 hour, 24 hours and 48 hours after the turpentine injection. After the tissue damage the rats move very little, huddle together, and do not groom themselves (as evidenced by very rough coats) for 2 to 3 days. In contrast, in the rats treated with GHL-Cu, nearly normal activity and grooming patterns return by 24 hours after the turpentine injection (Table 5).

TABLE 5

Beneficial effect of treatment with GHL-Cu on shock effects after traumatic tissue injury.

| Group and time | Number moving about cage |
|---|---|
| 24 hours post injury | |
| Control rats | 0 of 10 |
| GHL-Cu treated rats | 8 of 10 |

TABLE 5-continued

Beneficial effect of treatment with GHL-Cu on shock effects after traumatic tissue injury.

| Group and time | Number moving about cage |
|---|---|
| 25 hours post injury | |
| Control rats | 1 of 10 |
| GHL-Cu treated rats | 10 of 10 |
| 48 hours post injury | |
| Control rats | 4 of 10 |
| GHL-Cu treated rats | 10 of 10 |
| 49 hours post injury | |
| Control rats | 4 of 10 |
| GHL-Cu treated rats | 10 of 10 |

In addition, in the GHL-Cu treated animals the post-injury rise in the blood protein fibrinogen is reduced (Table 6). The acute-phase increase in blood fibrinogen after injury often complicates the recovery by increasing blood viscosity, and inducing red blood cell sludging and thromboembolitic episodes.

TABLE 6

Reduction in injury-induced increase in blood fibrinogen.

| | Fibrinogen concentration (mg/ml) |
|---|---|
| Control rats (6) | 2.8 ± 0.3 |
| Injured rats (6) | 5.3 ± 0.5 |
| Injured rats + GHL-Cu (6) | 3.9 ± 0.4 |

Statistical significance: (Injured rats vs. Injured rats & GHL-Cu), $p < 0.001$

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

What is claimed is:

1. A method for enhancing the wound-healing process in an animal comprising administering to the animal a therapeutically effective amount of a composition containing glcyl-L-histidyl-L-lysine: copper(II).

2. The method of claim 1 wherein said composition is administered through intravenous injection, topical application, or injection into the wound or the area surrounding the wound.

3. The method of claim 1 wherein said composition further includes an effective amount of dimethylsulfoxide.

4. The method of claim 1 wherein said composition is admixed with a pharmaceutically acceptable vehicle prior to being administered to said animal.

5. The method of claim 4 wherein said pharmaceutically acceptable vehicle is phosphate-buffered saline at a physiological pH.

6. A method of treating inflammatory conditions in animals comprising administering to the animal an antiinflammatorily effective amount of a composition containing glycyl-L-histidyl-L-lysine: copper(II).

7. The method of claim 6 wherein said composition is administered through intravenous injection, topical application, or injection into the wound or inflamed area, or the area surrounding the wound or inflamed area.

8. The method of claim 6 wherein said composition further includes an effective amount of dimethylsulfoxide.

9. The method of claim 6 wherein said composition is admixed with a pharmaceutically acceptable vehicle prior to being administered to said animal.

10. The method of claim 9 wherein said pharmaceutically acceptable vehicle is phosphate-buffered saline at a physiological pH.

11. A method of inhibiting a rise in blood fibrinogen in injured animals comprising administering to the animal a therapeutically effective amount of a composition containing glycyl-L-histidyl-L-lysine: copper(II).

12. The method of claim 11 wherein said composition is administered through intraveneous injection, or intraperitoneal injection.

13. The method of claim 11 wherein said composition further includes an effective amount of dimethylsulfoxide.

14. The method of claim 11 wherein said composition is admixed with a pharmaceutically acceptable vehicle prior to being administered to said animal.

15. The method of claim 14 wherein said pharmaceutically acceptable vehicle is phosphate-buffered saline at a physiological pH.

16. A method of reducing hyperfibrinogenemia, thromboembolism, shock or loss of ambulatory desires in animals occuring subsequent to major tissue damage, comprising administering to the animal an effective amount of a composition containing glycyl-L-histidyl-L-lysine: copper(II).

17. The method of claim 16 wherein said composition is administered through intraveneous injection, or intraperitoneal injection.

18. The method of claim 16 wherein said composition further includes an effective amount of dimethylsulfoxide.

19. The method of claim 16 wherein said composition is admixed with a pharmaceutically acceptable vehicle prior to being administered to said animal.

20. The method of claim 16 wherein said pharmaceutically acceptable vehicle is phosphate-buffered saline at a physiological pH.

* * * * *

UNITED STATES PATENT AND TRADEMARK OFFICE
CERTIFICATE OF CORRECTION

PATENT NO. : 4,760,051

DATED : July 26, 1988

INVENTOR(S) : Loren R. Pickart

It is certified that error appears in the above-identified patent and that said Letters Patent is hereby corrected as shown below:

On the cover page include the following:

Assignee: ProCyte Corporation

Attorney, Agent or Firm: SEED and BERRY

Signed and Sealed this

Twenty-fourth Day of January, 1989

Attest:

DONALD J. QUIGG

*Attesting Officer*  *Commissioner of Patents and Trademarks*